United States Patent [19]
Eisenschink et al.

[11] Patent Number: 5,231,014
[45] Date of Patent: Jul. 27, 1993

[54] FERMENTATION PROCESS FOR PRODUCING NATAMYCIN

[75] Inventors: Michael A. Eisenschink; Phillip T. Olson, both of Manitowoc

[73] Assignee: Bio-Technical Resources, Manitowoc, Wis.

[21] Appl. No.: 740,370

[22] Filed: Aug. 5, 1991

[51] Int. Cl.$^5$ .................. C12P 1/465; C12P 19/62; C12P 17/18
[52] U.S. Cl. .................. 435/76; 435/71.3; 435/118; 435/119; 435/242; 435/253.5; 435/886; 514/31; 536/6.5
[58] Field of Search ............ 435/76, 118, 119, 253.5, 435/71.3, 886, 242; 514/31; 536/6.5

[56] References Cited

U.S. PATENT DOCUMENTS 3,892,850  7/1975  Struyk et al.

FOREIGN PATENT DOCUMENTS

| 218265 | 3/1957 | Australia . |
| 669761 | 3/1957 | Canada . |
| 677040 | 7/1957 | Canada . |
| 844289 | 3/1957 | United Kingdom . |
| 846933 | 7/1957 | United Kingdom . |
| 2106498A | 7/1982 | United Kingdom . |

Primary Examiner—Herbert J. Lilling

[57] ABSTRACT

A natamycin producing Streptomyces species ferments to produce natamycin. A spore suspension of the Streptomyces species is propagated in a predetermined medium to obtain a quantity of Streptomyces cells. The Streptomyces cells ferment in a predetermined production medium having a controlled pH to produce a recoverable amount of natamycin.

28 Claims, 3 Drawing Sheets

FERMENTATION PROCESS FOR PRODUCING NATAMYCIN

BACKGROUND OF THE INVENTION

The present invention relates to a process for producing natamycin characterized by inoculum preparation, inoculum propagation and fermentation in a broth having a pH from about 5.0 through about 6.5.

Natamycin is a member of the polyene family of antimycotics. The compound natamycin is a tetraene with a molecular weight of about 666, empirical formula corresponding generally to $C_{33}H_{47}NO_{13}$, and it contains a glycosidically-linked carbohydrate moiety, mycosamine. Natamycin has an isoelectric point of about pH 6.5. The structure of natamycin exist typically in two configurations: the enol-structure and the keto-structure.

The production of natamycin has been known for years. A conventional fermentation process for producing natamycin is disclosed in American Cyanamid's British Patent No. 846,933 (1960). The disclosure of United Kingdom Patent No. 846,933 is hereby incorporated by reference.

Despite the antibiotic and anti-fungal value of natamycin, very little commercial use has been made of this product. One major reason for the limited use is the prohibitively high manufacturing cost of natamycin.

It is an object of the present invention to overcome the inefficiencies of conventional processes and provide a process for producing natamycin in a cost-effective manner by propagating and fermenting an inoculum in predetermined media having a controlled pH.

SUMMARY OF THE INVENTION

The present invention relates to fermentation by an organism capable of producing natamycin. Particularly the present invention is directed to preparing (e.g., sporulation) and propagating an inoculum comprising a Streptomyces species that, during fermentation, produces natamycin. The Streptomyces species is exposed to a series of predetermined environments and/or mediums which improve the rate at which natamycin is produced. It has been found that an enhanced rate of natamycin fermentation and improved yields can be achieved by adding sufficient amounts of basic pH control agents to the fermentation medium which maintain the pH between about 5.0 and 6.5.

A suitable aqueous medium for inoculum propagation comprises:

a) a protein nitrogen source in an amount of from about 2-16 g/l, normally about 8 g/l; and b) a metabolizable carbon source present in an amount which is sufficient to avoid total carbon depletion, usually 5-30 g/l of medium, and normally about 15 g/l.

A suitable aqueous medium used during fermentation to induce the inoculum to produce natamycin comprises:

a) about 80-250 g/l of a metabolizable carbon source; and b) a protein nitrogen source containing a high level of protein and trace ingredients. The protein nitrogen source typically comprises a non-yeast protein nitrogen component and a yeast protein nitrogen component. These two protein nitrogen components are desirably present in a ratio ranging, respectively, from about 5:1 to 11:1 based on protein contents, and for best results generally about 8:1.

DETAILED DESCRIPTION OF THE INVENTION

Figure 1:
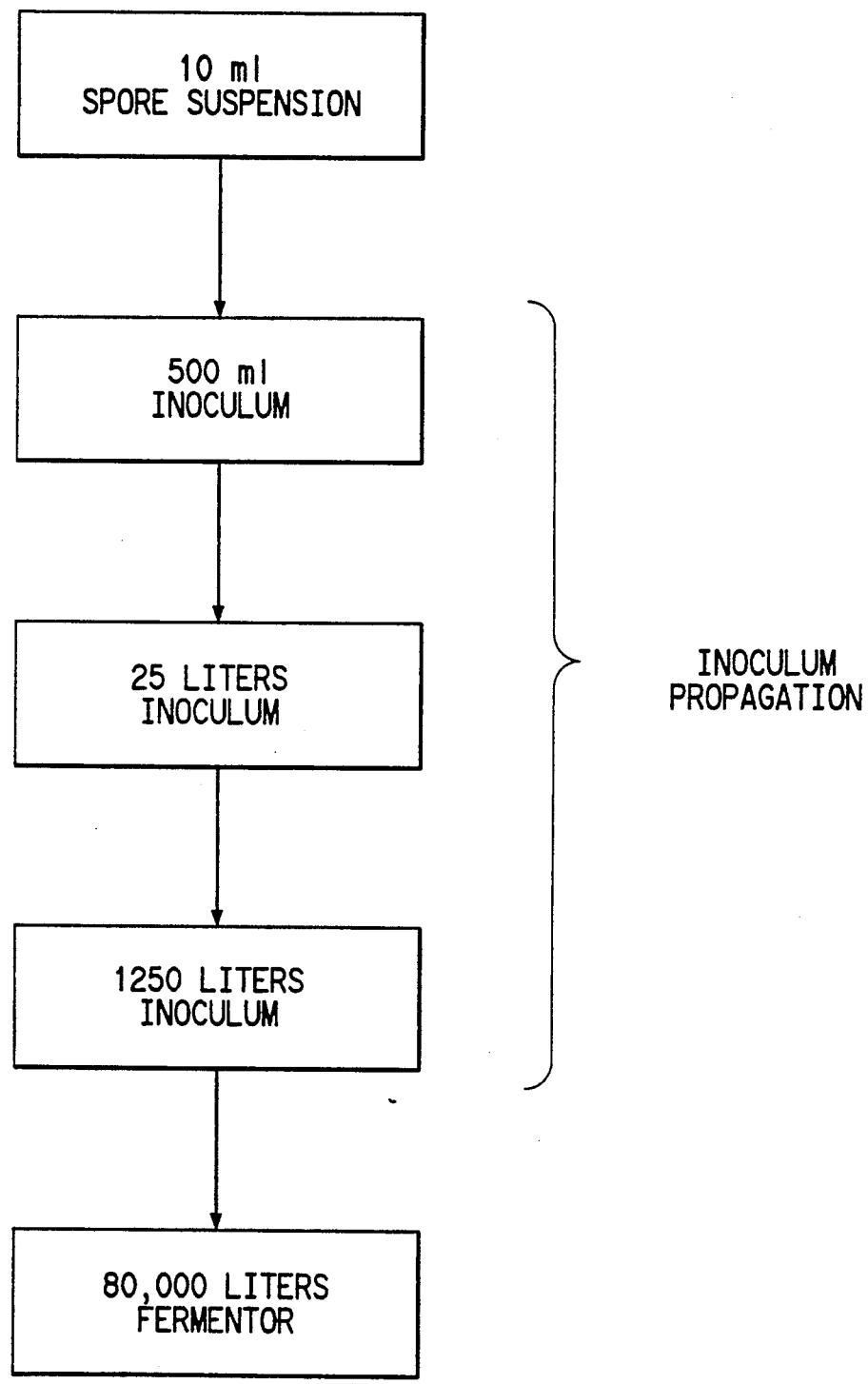
FIG. 1 is a schematic block diagram of the process which may be used in the invention for inoculum propagation.

In accordance with the present invention, an organism capable of producing natamycin is placed into contact with a predetermined medium to produce an inoculum, and then into a predetermined fermentation production medium that will support maximum metabolic activity of the organism during further propagation and natamycin producing fermentation. During fermentation the organism transforms at least a portion of the predetermined production medium into natamycin. It has been found that an enhanced rate of natamycin production and improved yields of natamycin can be achieved by adding sufficient amounts of basic pH control agents to the fermentation medium which maintain the pH between about 5.0 and about 6.5.

Any organism which comprises a natamycin producing Streptomyces species can be used in accordance with the invention. A preferred Streptomyces species comprises *Streptomyces gilvosporeus* which has been deposited previously with the American Type Culture Collection (ATCC) in Rockville, Md., United States of America, and is registered as ATCC No. 13326.

An inoculum is prepared from a spore suspension of the appropriate spores. The inoculum of the appropriate Streptomyces species is subsequently fermented which produces high yields of natamycin when placed into the fermentation medium of the invention. The inoculum is typically exposed to a series of propagation steps wherein each step increases the quantity of the natamycin producing Streptomyces cells. After the quantity of Streptomyces cells is adequate, the Streptomyces is exposed to an environment and/or a medium which is designed to enhance natamycin production when the Streptomyces species ferments.

Spore Suspension

The inoculum is started by collecting the spores of a natamycin producing Streptomyces species which was obtained from the American Type Culture Collection. The spores are germinated to produce an actively growing culture of the Streptomyces species. A sterilized (e.g., autoclaved), agar slant is inoculated heavily with the actively growing culture of the Streptomyces species (e.g., *Streptomyces gilvosporeus* or any other natamycin producing species), and incubated until the slant is covered substantially entirely with spores. The spores on the agar slant are scraped into a small amount of a liquid, such as water (e.g., distilled water), nutrient medium, etc., to produce an aqueous spore suspension. The resulting spore suspension is propagated to produce the inoculum for the fermentation operation (i.e., natamycin production). For achieving the best results, the spore suspension used to begin inoculum propagation should contain a spore concentration of about $10^5$–$10^{10}$ CFU/ml, and, normally, at least about $10^8$ CFU/ml.

A number of agar slant media can be used to promote sporulation of the culture of the Streptomyces species (e.g., *S. gilvosporeus*), which will be used to form the spore suspension. Appropriate agar slant mediums typically comprise at least one member of the following group: yeast malt agar, Hickey-Turner agar, GYA agar, Pridham agar, potato dextrose, Bennett's agar, etc.

A high concentration (e.g., $10^8$ CFU/ml), of viable spores within the spore suspension is a key aspect of the present invention. First, if the concentration of spores is too low, it takes much longer to obtain, through inoculum propagation, the quantity of Streptomyces cells sufficient for cost-effective natamycin fermentation production. Second, a reduced quantity of spores within the suspension lengthens the total inoculum propagation time and increases the likelihood of contamination (e.g., by an unwanted organism). Further, a low spore concentration within the suspension may tend to promote the formation of large, tightly packed mycelial pellets. These pellets are unsuitable for obtaining high yields of natamycin due to problems associated with oxygen transfer, mass transfer of nutrients into the pellets, etc. Should the size of mycelial pellets become undesirable, the pellets can be broken apart physically, such as by using a shear force (e.g., blending).

Inoculum Propagation

The aqueous spore suspension (e.g., *S. gilvosporeus*), discussed above, is germinated and cell multiplication continued until the number of organisms is adequate to be used as an aqueous inoculum for fermentation production of natamycin. A suitable inoculum cell density comprises a dry cell weight of about 1-5 g/l and is used at a volume of about 0.1-10% of the natamycin production medium volume.

The aqueous medium used for inoculum propagation determines the cell density and the metabolic state of the inoculum (e.g., an adequate density of healthy cells is desirable). A sufficient amount of protein nitrogen, which contains complex growth factors (e.g., vitamins), and inorganic elements (e.g., potassium, sodium, calcium, etc.), and trace elements (e.g., boron, cobalt, iron, copper, zinc, etc.), that are commonly present in the protein nitrogen source, are needed to achieve an inoculum possessing the desired cell density and metabolic state. The protein nitrogen source may be any source that will propagate the spore suspension into an inoculum that will produce the desired high yields of natamycin.

A metabolizable source of carbon must also be supplied to the aqueous inoculum medium in an amount which is sufficient to achieve the desired inoculum cell density. For best results, the carbon source should not be depleted completely during the inoculum propagation. Depletion of the carbon source tends to alter adversely the metabolic state of the inoculum, which may lead to reduced yields of natamycin during fermentation.

Although a variety of aqueous inoculum media can be used effectively in accordance with the present invention, to obtain high yields of natamycin it is advantageous to use predetermined amounts of medium ingredients.

A suitable medium for inoculum propagation may be prepared in water (e.g., low mineral content water, distilled water, etc.), and comprises:

a) a protein nitrogen source in an amount from about 2-16 g/l, normally about 8 g/l; and
b) a metabolizable carbon source present in an amount which is sufficient to avoid total carbon depletion, usually 5-30 g/l of medium, and normally about 15 g/l.

Two specific compositions of a medium appropriate for inoculum propagation are given below.

|  | Quantity |
|---|---|
| Composition 1 | |
| Difco "Bacto" peptone | 5 g/l |
| Corn steep liquor | 3 g/l |
| Sodium chloride | 10 g/l |
| Glucose | 15 g/l |
| Composition 2 | |
| Hormel peptone PSR 5 | 8 g/l |
| Sodium chloride | 10 g/l |
| Glucose | 15 g/l |

The inoculum medium which provides nutrients that enhances the production rate of Streptomyces cells may be prepared by conventional techniques (e.g., separate or simultaneous sterilization of the carbon and nitrogen sources at temperatures of about 120°–140° C.). The inoculum medium after sterilization, desirably has a pH of about 7. The spore suspension is introduced to the inoculum medium and the inoculum medium is heated to a temperature of about 25°–40° C. and, normally, about 28°–35° C.

In order to achieve the large volumes of aqueous inoculum which are desirable for fermentation production of natamycin, several inoculum propagation steps are required, each carried out in a volume greater than the previous step. For example, the inoculum propagation may be conducted in a manner which achieves an exponential increase in the quantity of Streptomyces cells. Particularly, it is advantageous to keep the culture in an exponential growth mode during propagation by effectively increasing the volume of the inoculum during each step of the propagation. This can be done by either minimizing the duration of each step or by minimizing the number of steps. For example, once a predetermined cell density of inoculum has been achieved, the inoculum is transferred to a larger environment (e.g., vessel), for further propagation. By effectively controlling the inoculum propagation a minimum of time and expense is devoted to inoculum propagation and, accordingly, cost-effective natamycin yields during fermentation are increased.

The length of time an individual step in the series of inoculum propagation steps is permitted to continue depends upon the composition of the medium, quantity of Streptomyces cells desired, temperature, etc. Typically, an individual propagation step is conducted for about 6 through at least about 24 hours.

The inoculum propagation process requires aeration of the inoculum. For example, the flask or vessel housing the inoculum may be agitated on a rotary shaker at about 200 rpm. In one aspect of the invention, the inoculum may be agitated by an impeller which is located within the vessel that houses the inoculum, while sterile air is forced into the bottom of the vessel.

Now referring to FIG. 1, this figure is a schematic of the process which may be used to produce the inoculum that is fermented to produce nataymcin. FIG. 1 illustrates the volumetric increases in the inoculum which are typically achieved by propagation that are necessary to obtain a quantity of aqueous inoculum that is adequate to produce natamycin in a cost-effective manner. For example, the volume of inoculum is increased from 25 liters to 1250 liters by adding the 25 liters of inoculum to a vessel containing 1225 liters of an aqueous inoculum medium.

Natamycin Production

Natamycin production is conducted in a fermentation vessel which is capable of housing the fermentation process. It has been found that an enhanced rate of natamycin fermenation and improved yields can be achieved by adding sufficient amounts of basic pH control agents to the fermentation medium which maintain the pH between about 5.0 and about 6.5. One aspect of the invention which is also important for achieving maximum yields of natamycin is the composition of the aqueous fermentation medium. The fermentation medium must contain the proper amounts of metabolizable carbon and protein nitrogen. Also, it is desirable that the medium include complex growth factors (e.g., vitamins), inorganic elements (e.g., potassium, sodium, calcium, etc.), and trace elements (e.g., boron, cobalt, iron, copper, zinc, etc.)

A suitable medium for fermentation may be prepared in water (e.g., low mineral content water, distilled water, etc.), and comprises:

a) about 80-250 g/l of a metabolizable carbon source; and b) at least about 15 g/l and, normally about 20 g/l through 80 g/l, of a protein nitrogen source containing a high level of protein and trace ingredients. The protein nitrogen source may comprise a non-yeast protein nitrogen component and a yeast protein nitrogen component. These two protein nitrogen components are usually present in the ratio ranging, respectively, from about 5:1 to 11:1 based on protein contents, and for best results generally about 8:1.

The protein nitrogen source may be supplied from a wide range of sources. For example, soy protein products may comprise the non-yeast protein nitrogen source (e.g., desirable natamycin yields are obtained with a soy protein source comprising 80-95% protein). The protein nitrogen may also comprise beef extract and/or protein hydrolysates (e.g., peptones).

As discussed above, the production medium must also include a source of carbon which is metabolizable by the Streptomyces species. The carbon source may be supplied in any expedient form such as glucose, polysaccharide, corn and potato starches, etc.

Moreover, in one aspect of the invention, it is not necessary to initially introduce the entire quantity of the carbon source which is required to produce natamycin, as a starting component of the natamycin production medium (e.g., the initial quantity of the carbon source is not adequate for complete fermentation). In this aspect of the present invention, carbon source addition may be performed during the natamycin production so as to maintain a quantity of carbon source of about 5-30 g/l, and usually 20 g/l. Thus, an appropriate quantity of a suitable carbon source is added to the fermentation medium either initially and/or after the fermentation has begun. For example, the carbon source may be present in the fermentation medium in an amount of about 40-100 g/l. Thereafter, during the major period of fermentation, carbon source is continually added to the fermentor at a rate which is at least equivalent to the rate at which the carbon source is consumed enzymatically by the Streptomyces species during the fermentation process(e.g., to maintain the carbon source concentration at or above a minimum level). Toward the end of the fermentation process and after the major fermentation period, the carbon source addition is discontinued so that little or no carbon source is left at the end of the fermentation cycle (e.g., the quantity of the carbon source substantially equates to the particular quantity of carbon source within the fermentation medium which is necessary to complete the fermentation process).

The natamycin production medium, which provides nutrients for the Streptomyces fermentation and natamycin production may be prepared by conventional techniques (e.g., separate or simultaneous sterilization of the carbon and nitrogen sources at temperatures of about 120°-140° C.). The production medium, after sterilization, desirably has a pH of about 7.

The inoculum is introduced until a concentration of about 0.1-10%, usually about 2%, by volume is achieved in the production medium (e.g., the quantity of inoculum may be sufficient to inoculate a plurality of fermentors). The remainder of the volume of the fermentor comprises the fermentation medium discussed above. Any technique is acceptable for introducing the inoculum to the production medium within the fermentor which delivers the inoculum in an active metabolic state.

The fermentation or production medium is brought to a temperature of about 25°-40° C., and normally about 28°-35° C. The length of time which the fermentation process is allowed to continue depends upon the composition of the fermentation medium, temperature, quantity of Streptomyces cells in the inoculum, quantity of natamycin desired, etc. Typically, the fermentation process is conducted for about 70 through at least about 168 hours.

Oxygen is supplied to the natamycin production medium during fermentation. It is advantageous to maintain a dissolved oxygen level in the production medium of about 20%-80% of air saturation during the major portion of the fermentation. The ability to achieve a suitable dissolved oxygen level may be enhanced by proper adjustment of the aeration and/or agitation rate. For example, the fermentation or production medium must be aerated by forcing air (e.g., sterile air), through the fermentation medium, usually at a rate of about 0.3 through at least about 1.0 volumes of air per volume of fermentation medium. In one aspect of the invention it is desirable to agitate the fermentation medium while being aerated. Further, the rate of aeration may be sufficient to cause agitation of the fermentation medium.

Figure 2:
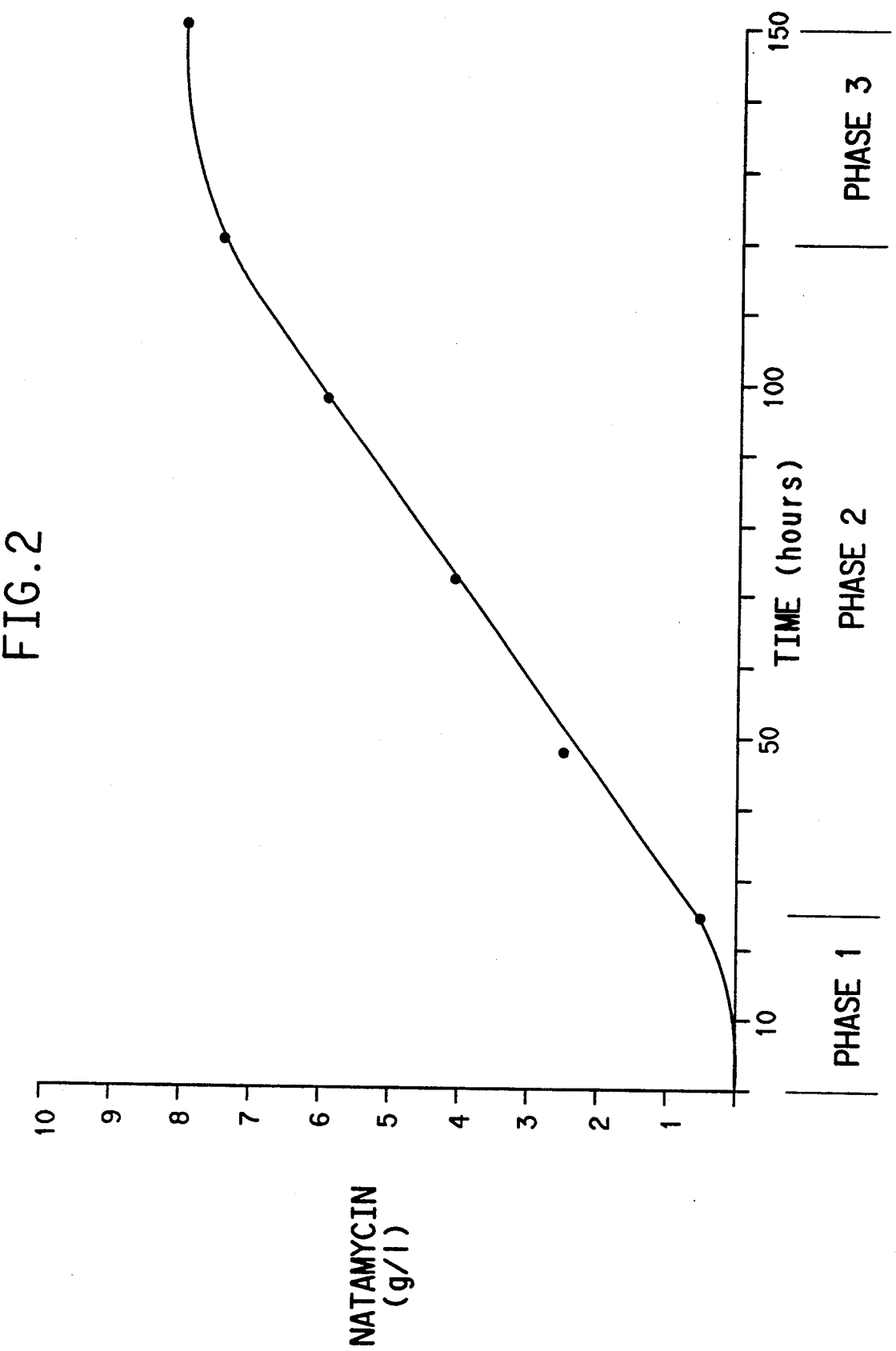
FIG. 2 is a graphical representation of the three phases which typically occur during fermentation.

Referring now to FIG. 2, the relationship between time and nataymcin production rates is shown for each of the three phases of the process. The first phase includes addition of the carbon source to the fermentation medium and growth or multiplication of the Streptomyces species. The first phase is also accompanied by natamycin production. The concentration of natamycin in the fermentation broth increases as the propagation of the cells of the Streptomyces species increases. The increase in the concentration of natamycin increases generally exponentially with time during the first phase. Eventually, the concentration of natamycin will increase constantly with time, which indicates that the second phase (i.e., the major phase) of natamycin production as been achieved. The third phase is characterized by a plateau in the concentration of natamycin (e.g., which may be due to a slowing of the metabolic activities of the Streptomyces species). The concentration of natamycin within the fermenter may be analyzed with respect to time in order to ascertain the current phase of fermentation. It is desirable to use a medium and/or an environment which induces the second phase of fermentation to be reached rapidly and maintained in order to maximize the overall quantity of natamycin that is produced.

In one aspect of the invention, it may be desirable to add an anti-foaming agent (e.g. silicone defoamer), to the fermentation medium in an amount of from about 0.01%–1% by volume of the fermentation or natamycin production medium when it is desirable to control foaming.

The natamycin production medium after inoculum addition has a pH of about 7. As discussed above, during the relatively short first phase of fermentation, rapid culture propagation is the major activity. Thereafter natamycin production becomes the predominant activity, and the pH drops. Controlling or maintaining the pH during fermentation is a key aspect of the invention because, without pH control, the pH will drop to about pH 4.0 during natamycin production.

The major or second phase of natamycin production corresponds to the period beginning when the pH has first dropped below about pH 6.5 until near the end of the natamycin production. Toward the end of the fermentation the pH may be allowed to drop below about pH 5.0. In accordance with the invention, the major phase does not include this low pH period when the pH is below about pH 5.0.

The pH of the fermentation broth which comprises the fermentation medium may be controlled by adding pH control agents to the broth. The pH control agents used in the process of the invention comprise hydroxides and basic salts that will control the pH without adversely affecting the natamycin production and recovery. Suitable pH control agents comprise at least one of sodium potassium and calcium hydroxides, and mono-, di- and trisodium and potassium citrates, etc.

In accordance with the invention, the pH of the fermentation cycle is allowed to drop initially, (i.e., during culture propagation), to about pH 6. By this time effective natamycin production is underway. After the pH has dropped into the range of from about pH 5.0 to about 6.5, addition of the basic pH control agent is commenced and continued at rates sufficient to maintain the fermentation broth thereafter at a pH of about 5.0 through about 6.5. Normally, the pH is maintained by automatic pH controlled titration with an aqueous solution including the pH control agent.

A variety of pH control agent compositions, blends, mixtures, etc., can be used simultaneously and/or sequentially. For example, it may be desirable to introduce both a citrate salt and a hydroxide into the fermentation broth (e.g., a hydroxide could be added simultaneously to more easily maintain a pH of about 5.0–6.5). However, in some aspects of the invention, an acidic citrate can be added in conjunction with a basic pH control agent.

A key aspect of the invention comprises using a pH control agent comprising an inorganic base to maintain a pH of about 5.9–6.1. As aforementioned, the pH control of the present invention enhances the rate of natamycin production and improves the yield of natamycin. For example, the pH control of the invention may permit fermentation production of natamycin in far less time in comparison to an equivalent yield of natamycin produced without pH control. Typically, the production time is decreased 20–60%, with a reduction of about 35% being common.

When the present invention is practiced appropriately (e.g., effective handling of the Streptomyces inoculum, selection of media, etc.), the resultant fermentation broth will normally include at least about 5 g/l of natamycin. In certain cases, the level of natamycin production may range from about 7 g/l through at least about 12 g/l.

The natamycin can be separated from the production medium. In certain cases, the natamycin may be extracted from the fermentation broth and crystallized. Examples of acceptable techniques for obtaining crystalline natamycin can be found in U.K. Patent No. 846,933.

The invention is demonstrated by the following Example which is intended to illustrate, not limit, the scope of contemplated equivalents. Unless specified otherwise, commercially available reagent grade materials were used to conduct the following Example.

EXAMPLE

In the following tests, agar slants of the following compositions are prepared using distilled water.

| | |
|---|---|
| 3 g/l | yeast extract (Difco "Bacto" Yeast Extract) |
| 3 g/l | malt extract (Difco Malt Extract) |
| 5 g/l | peptone (Difco "Bacto" peptone) |
| 10 g/l | glucose |
| 15 g/l | agar. |

The agar was sterilized at about 121'C for about 15 minutes.

An inoculum medium of the following composition was prepared in distilled water, and the pH was adjusted to about 7.0 with potassium hydroxide.

| | |
|---|---|
| 20 g/l | glucose |
| 10 g/l | sodium chloride |
| 6 g/l | corn steep liquor (PPM (brand), Corn Steep Liquid) |
| 6 g/l | peptone (Difco "Bacto" peptone) |

The inoculum medium was sterilized at about 121'C for about 15 minutes.

*Streptomyces gilvosporeus*, American Type Culture Collection Registration No. 13326, was obtained from the American Type Culture Collection as a freeze-dried spore suspension and used as the culture source. The culture was held on the agar slants at about 25'C until the culture sporulated.

The agar slants sporulated heavily within about 10 days and were used after 10–20 days. Spores were scraped off these agar slants into the inoculum medium to achieve a spore suspension concentration of about $10^8$ CFU/ml. About 2 ml of the spore suspension was added to about 100 ml of the inoculum medium in a 500 ml baffled flask. The inoculum in the baffled flask was incubated for about 48 hours at about 29° C. and agitated at about 200 rpm on a rotary shaker. After about 48 hours about 4 ml of this culture was added to about 200 ml of inoculum medium in a 1000 ml baffled flask, to propagate the inoculum. This inoculum was then incubated for about an additional 24 hours at about 29° C. and agitated at about 200 rpm on a rotary shaker. The inoculum thus produced was used to inoculate 8 l of production medium.

The natamycin production medium used in this Example was of the following initial composition:

| | |
|---|---|
| 19.5 g/l | soy protein isolate (ADM, "Profam" S970) |
| 4.5 g/l | yeast extract (Stauffer, Type KAT) |
| 0.2 ml | defoamer (Mazu, DF 289) |

The production medium was prepared in distilled water in a 14.0 l fermenter and the pH was adjusted to about 7.6 with potassium hydroxide. The fermenter was then sterilized for about 15 minutes at about 121° C. Glucose was sterilized separately as a 50% solution in distilled water.

Before inoculation, the production medium was heated to about 29° C. and the glucose was added to achieve an initial concentration of glucose of about 40 g/l. An aeration rate of about 0.3 v/v-min. (volumes of air per volume of medium per minute) and an agitation rate of about 300 rpm was established for the fermentor.

The inoculum discussed above containing *Streptomyces gilvosporeus*, (ATCC Registration No. 13326), was added to the fermentation vessel until the fermentation vessel had an inoculum content of about 2% by volume. Glucose was added to the inoculum after about 40 hours of fermentation in order to maintain a glucose concentration of about 20 g/l glucose in the fermentation vessel. This was done by feeding glucose to the fermenting vessel at a rate of about 1 g/l-hr. The agitation rate of the fermentation vessel was increased as necessary to maintain a dissolved oxygen level of about 50% of air saturation.

Test #1—This test shows the typical practice of the high yield fermentation process, but without the pH control of the present invention. Proceeding as described above, starting with an initial volume of about 8.0 l production medium (pH of about 7) and continuing the fermentation cycle time for about 117 hours (pH of about 4.5), with a total glucose addition of about 110 g/l, a yield of about 7.3 g/l natamycin in about 8.7 l of fermentation broth was obtained (64 g natamycin, total).

Test #2—Proceeding substantially as in Test #1, but after 18 hours when pH had dropped to about 6.0 adding about 20% KOH to maintain the pH at about 6.0, and adding about 155 g/l glucose over the cycle of about 92 hours there is obtained a natamycin yield of about 7.4 g/l in about 10.1 l (75 g natamycin, total). Thus, as compared to Test #1, this test of the present invention provides an equivalent yield of natamycin in a shorter production period.

By following substantially the same procedure but using NaOH instead of KOH, similar rapid high yield natamycin production was achieved.

Test #3—Continuing production of Test #2 and adding about 250 g/l glucose over about a 282 hour total fermentation cycle time there was obtained a natamycin yield of about 12.4 g/l in about 10.4 l of fermentation broth (129 g natamycin, total). Thus, prolonged natamycin production is possible to give high natamycin yields.

Test #4—Proceeding as in Test #2, but when the pH decreased to about pH 6, about 20% potassium hydroxide was added by automatic titration to maintain a pH of about 6.1-5.9. After about 66 hours fermentation time, about 6.6 g/l of natamycin was produced in about 9.2 l fermentation broth (61 g natamycin, total).

Test #5—Proceeding as in Test #2, but at about 24 hours when the fermentation broth was at a pH of about 5.1, about 7 g/l of trisodium citrate was added to the fermentation vessel. The pH remained in a pH range from about 5.0 to 6.5. Fermentation was continued for about 69 hours. Production of natamycin was about 6.6 g/l in about 8.7 l (57 g natamycin, total).

By following substantially the same procedure but using an equimolar amount of tripotassium citrate, similar rapid high yield natamycin production was achieved.

Test #6—By proceeding substantially in accordance with Test #5 except that in place of the trisodium citrate pH control agent, there was added at about 24 hours after the start of fermentation trisodium citrate adjusted to a pH of about 5.0 with citric acid (this addition contained about 5 g/l of citrate ion); then after about 45 hours citric acid was added to maintain pH below about 5.0. Only about 25.6 g of natamycin was produced after about 117 hours of fermentation.

Test #7—Proceeding substantially in accordance with Test #1 but without the addition of any pH control agent, after about 66 hours of fermentation the natamycin yield was only 4.3 g/l in about 8.3 l broth (36 g natamycin, total). A comparison of Test #4 and Test #7 illustrates that pH control will enhance the natamycin production rate (i.e., the 66 hour fermentation process of Test #4 produced 61 g of natamycin whereas Test #7 produced only 36 g of natamycin).

The following Table summarizes the results of Tests 1-7 in terms of relative speed of natamycin production. A review of the following Table demonstrates that the pH control of the invention improves the yield of natamycin obtained via a fermentation process.

TABLE

| Test # | pH Control Agent | Production Time (hrs) | Quantity Natamycin Produced (Total/Concentration) |
|---|---|---|---|
| 1 | None | 117 | 64 g/7.3 g/l |
| 2 | KOH | 92 | 75 g/7.4 g/l |
| 3 | KOH | 282 | 129 g/12.4 g/l |
| 4 | KOH | 66 | 61 g/6.6 g/l |
| 5 | Trisodium citrate | 69 | 57 g/6.6 g/l |
| 6 | Trisodium citrate/ Citric Acid | 117 | 25.6 g/3.2 g |
| 7 | None | 66 | 36 g/4.3 g/l |

Figure 3:
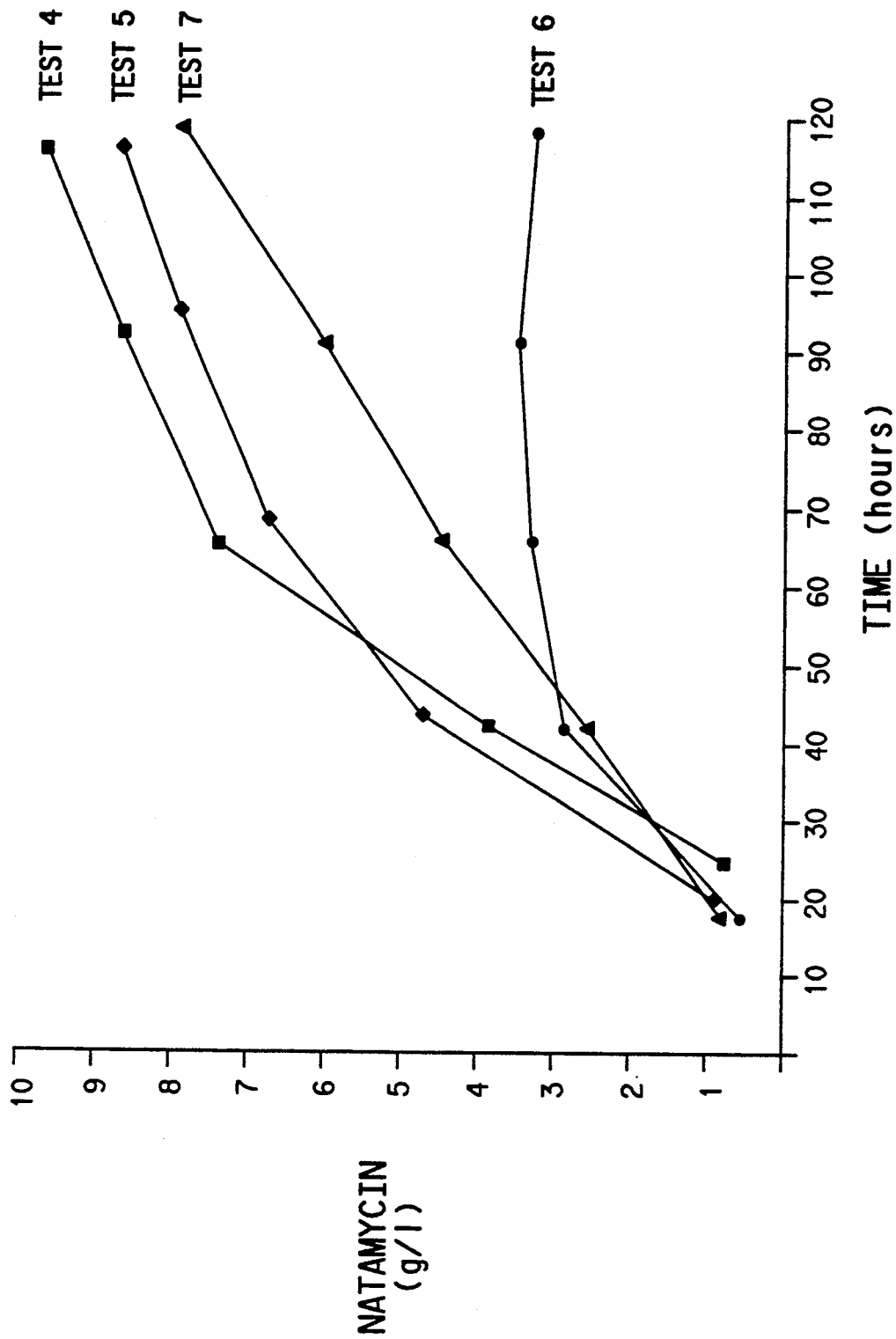
FIG. 3 is a graph of time vs. natamycin production for the natamycin produced in accordance with Tests 4 through 6 of the Example.

Now, refer to FIG. 3, which is a graph illustrating the natamycin production (g/l in the fermentation broth) over about 115 hours of the fermentation process which was performed in accordance with Tests 4, 5, 6 and 7. A review of FIG. 3 illustrates graphically that the pH control of the invention enhances the rate at which natamycin is produced.

Although a few embodiments of the invention have been described above in detail, those skilled in this art will readily appreciate that the present invention embraces many combinations and variations.

What is claimed:

1. In a process for preparing natamycin including the steps of (a) obtaining an inoculum by propogating a spore suspension containing a natamycin-producing Streptomyces species in an inoculum medium; (b) introducing the inoculum to a fermentation medium and providing a fermentation broth comprising said fermentation medium and inoculum; (c) producing natamycin by a fermentation in said fermentation broth; and (d)

recovering natamycin produced by said fermentation, an improvement comprising:

in (c) using a fermentation with a cell propogation stage followed by major natamycin production stage, adding a basic pH control agent at a rate sufficient to maintain the fermentation broth at a pH of from 5.0 to 6.5 during said major natamycin production stage, and continuing the fermentation to provide a fermentation broth containing at least about 5 g/l natamycin.

2. The process of claim 1 wherein said natamycin producing species comprises *Streptomyces gilvosporeus*, ATTCC 13326.

3. The process of claim 1 wherein said spore suspension contains a spore suspension of at least $10^5$–$10^{10}$ CFU/ml.

4. The process of any one of claims 1 or 2 wherein said fermentation medium contains non-yeast and yeast protein nitrogen components, said non-yeast and yeast components being present in the ratio ranging, respectively, from about 5:1 to 11:1 based on protein contents.

5. The process of any one of claims 1 or 2 wherein the inoculum medium comprises from about 2 through about 16 g/l of a protein nitrogen source and about 5 through 30 g/l of a carbon source.

6. The process of any one of claims 1 or 2 wherein the fermentation medium comprises from about 80 through about 250 g/l of a carbon source and nitrogen source; wherein the nitrogen source further comprises a non-yeast component and a yeast component.

7. The process of claim 6 wherein the ratio of non-yeast and yeast components of said protein nitrogen source ranges from about 5:1 through about 11:1, based on a protein content.

8. The process of claim 7 wherein said non-yeast component of said protein nitrogen source comprises soy protein.

9. The process of any one of claims 1 or 2 wherein the concentration of carbon source in the fermentation medium is maintained at about 5–30 g/l during the major natamycin production period.

10. The process of any one of claims 1 or 2 wherein at least 7 g of natamycin is produced per liter of fermentation medium.

11. The process of any one of claims 1 or 2 wherein the propagation and fermentation are conducted at temperature of from about 25 to about 40 degrees C.

12. The process of any one of claims 1 or 2 wherein the fermentation is conducted for a period of time from about 70 through at least about 168 hours.

13. The process of any one of claims 1 or 2 further comprising aerating the inoculum during propagation and fermentation.

14. The process of any one of claims 1 or 2 further comprising aerating the inoculum during natamycin production.

15. The process of any one of claims 1 or 2 wherein the inoculum and fermentation media include a carbon source which comprises at least one member from the group consisting of glucose, saccharide and starch.

16. The process of any one of claims 1 or 2 wherein the inoculum and fermentation media include a protein nitrogen source which comprises at least one member from the group consisting of soy protein, yeast and protein hydrolysate.

17. The process of claim 15 wherein the protein nitrogen source comprises a soy protein comprising at least one member from the group consisting of isolates, flours and meals.

18. The process of claim 15 wherein the protein nitrogen source comprises a yeast comprising at least one member from the group consisting of whole yeast extracts and autolysates.

19. The process of any one of claims 1 or 2 further comprising using a pH control agent comprising at least one member of the group consisting of hydroxides and citrates.

20. The process of claim 1 wherein carbon source is provided in the fermentation medium at from about 80 g/l to 250 g/l; wherein the carbon source addition is performed during the natamycin production stage so as to maintain a quantity of carbon source of from about 5 g/l to 30 g/l; wherein at least about 15 g/l at a protein nitrogen source is provided in the fermentation medium; wherein the protein nitrogen source comprises a non-yeast protein nitrogen component and a yeast protein nitrogen component; and wherein the ratio of non-yeast protein nitrogen component to yeast protein nitrogen component is from about 5:1 to 11:1, based upon protein content.

21. The process of claim 1 or claim 20 wherein the dissolved oxygen level is maintained at from about 20% to 80% of air saturation during said major natamycin production stage.

22. The process of claim 21 wherein the fermentation is continued until the fermentation broth includes from about 5 g/l to 12 g/l natamycin.

23. The process of claim 1 wherein the inoculum is introduced in (b) in a concentration of from about 0.1 to 10 volume percent of the fermentation broth.

24. The improved process of claim 23 wherein the inoculum introduced in (b) has a cell density based upon a dry cell weight, of from about 1 to 5 g/l.

25. The process of claim 1 wherein (a), a spore suspension containing a spore concentration of at least about $10^8$ CFU/ml is propogated to obtain said inoculum.

26. The process of claim 1 or claim 25 wherein in (a) the inoculum is obtained using a series of propogation steps comprising propagating cells in one inoculum medium to achieve one inoculum having a selected range of cell density, then transferring said one inoculum to another inoculum medium of greater volume and further propagating cells to achieve larger inoculum having said selected range of cell density, and then transferring the said larger inoculum to yet another inoculum medium at yet greater volume and further propogating cells to achieve a yet larger inoculum having said selected range of cell density.

27. The process of claim 26 wherein said selected range of cell density is from about 1 g/l to 5 g/l, based upon dry cell weight.

28. The improved process of claim 1 wherein the fermentation has a natamycin plateau stage following said major natamycin production stage; and wherein the pH is allowed to drop below 5 during the natamycin plateau stage.

* * * * *